(12) United States Patent
Paul et al.

(10) Patent No.: US 7,856,275 B1
(45) Date of Patent: Dec. 21, 2010

(54) VESTIBULAR SYSTEM STIMULATION APPARATUS

(75) Inventors: Zachary Paul, Pittsburgh, PA (US); Stefanie Lattner, Gibsonia, PA (US); Stefanida K. Blake, Jamaica Plain, MA (US); Patrick Devinney, Pittsburgh, PA (US); Mark DiMatteo, Irwin, PA (US); Steven B. Radney, Pittsburgh, PA (US); Peter Chi Fai Ho, Pittsburgh, PA (US); Benjamin A. Giovannelli, Stahlstown, PA (US); Michael Cessna, Pittsburgh, PA (US); Michael E. Colbaugh, Trafford, PA (US)

(73) Assignee: Ric Investments, LLC, Wilmington, DE (US)

( * ) Notice: Subject to any disclaimer, the term of this patent is extended or adjusted under 35 U.S.C. 154(b) by 909 days.

(21) Appl. No.: 11/327,062

(22) Filed: Jan. 6, 2006
(Under 37 CFR 1.47)

Related U.S. Application Data

(60) Provisional application No. 60/642,367, filed on Jan. 7, 2005.

(51) Int. Cl.
*A61N 1/36* (2006.01)

(52) U.S. Cl. ...................................... 607/55

(58) Field of Classification Search ............. 607/55–57
See application file for complete search history.

(56) References Cited

U.S. PATENT DOCUMENTS

| | | | | |
|---|---|---|---|---|
| 3,274,994 A | * | 9/1966 | Sturm | 600/549 |
| 4,558,703 A | | 12/1985 | Mark | |
| 4,592,370 A | * | 6/1986 | Lee et al. | 600/379 |
| 4,601,294 A | * | 7/1986 | Danby et al. | 600/379 |
| 4,622,975 A | * | 11/1986 | Danby et al. | 600/379 |
| 4,741,344 A | * | 5/1988 | Danby et al. | 600/379 |
| 5,213,099 A | | 5/1993 | Tripp, Jr. | |
| 5,673,692 A | | 10/1997 | Schulze et al. | |
| 5,712,917 A | * | 1/1998 | Offutt | 381/328 |
| 5,958,625 A | * | 9/1999 | Rao | 429/241 |
| 6,077,237 A | | 6/2000 | Campbell et al. | |
| 6,219,578 B1 | | 4/2001 | Collins et al. | |
| 6,228,021 B1 | | 5/2001 | Kania | |

(Continued)

FOREIGN PATENT DOCUMENTS

DE    3910749 A1    10/1990

OTHER PUBLICATIONS

Gilbert et al., "Thermoregulation as a sleep signalling system", Sleep Medicine Reviews, 2004, pp. 81-93, Elsevier Ltd.

(Continued)

*Primary Examiner*—Scott M Getzow
*Assistant Examiner*—Amanda Patton
(74) *Attorney, Agent, or Firm*—Timothy A. Nathan

(57) ABSTRACT

Apparatus for the non-invasive and specific activation of the vestibular system in a patient. Preferred embodiments of the present invention allow for the placement of a stimulating electrode in the ear canal while providing a firm and comfortable coupling with the patient. The stimulating electrode is a deformable material that contacts the skin in the ear canal. A stimulating device operates in cooperation with the stimulating electrode to generate a stimulation waveform for the stimulation of the vestibular system.

18 Claims, 11 Drawing Sheets

U.S. PATENT DOCUMENTS

| | | | |
|---|---|---|---|
| 6,253,871 B1 | 7/2001 | Aceti | |
| 6,314,324 B1 | 11/2001 | Lattner et al. | |
| 6,640,121 B1 * | 10/2003 | Telischi et al. | 600/379 |
| 7,225,028 B2 * | 5/2007 | Della Santina et al. | 607/57 |
| 2003/0195588 A1 * | 10/2003 | Fischell et al. | 607/55 |
| 2004/0138723 A1 * | 7/2004 | Malick et al. | 607/57 |
| 2005/0033384 A1 * | 2/2005 | Sacha | 607/57 |
| 2006/0094974 A1 * | 5/2006 | Cain | 600/544 |

OTHER PUBLICATIONS

Fitzpatrick et al., "Probing the human vestibular system with galvanic stimulation", J Appl Physiol, 2004, pp. 2301-2316, 96, the American Physiological Society.

* cited by examiner

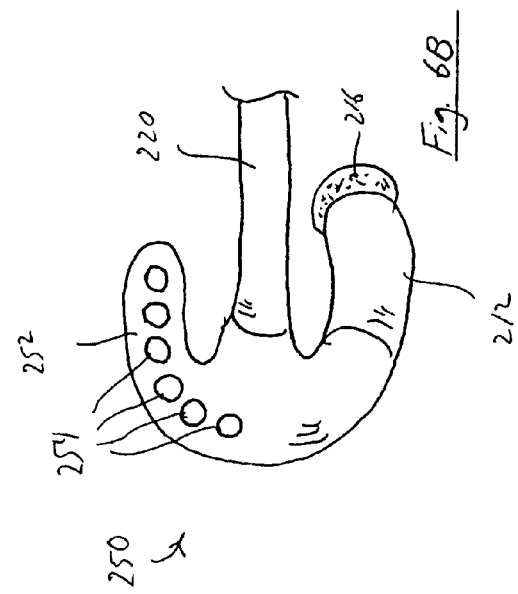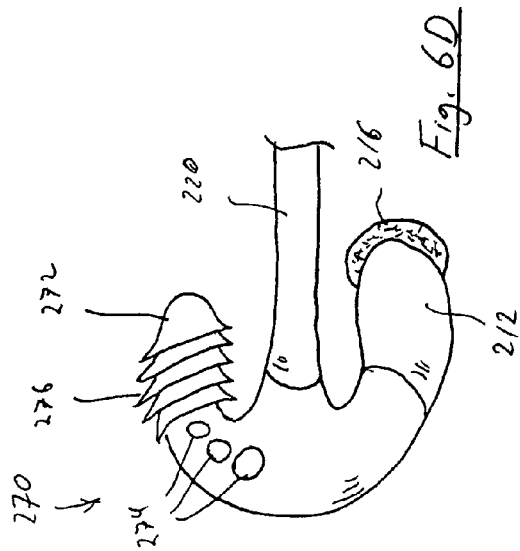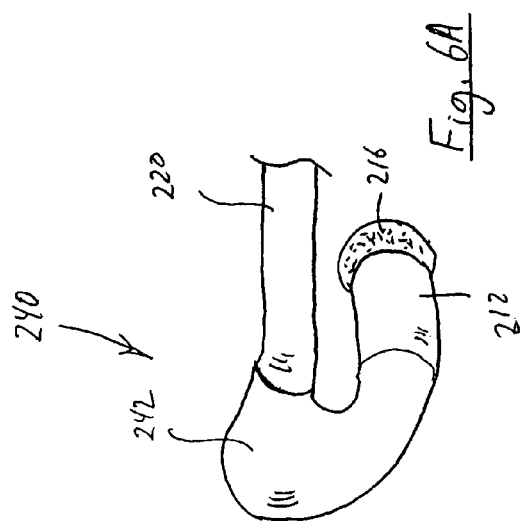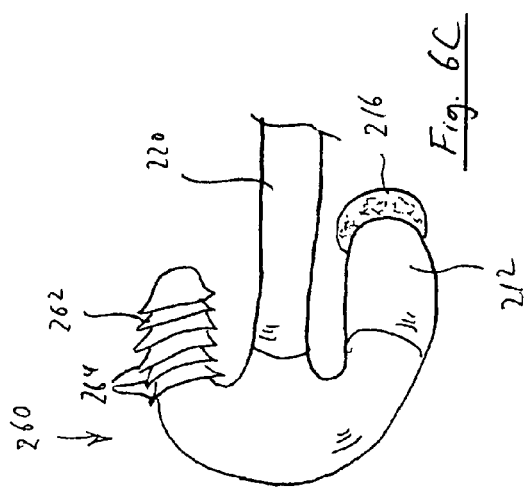

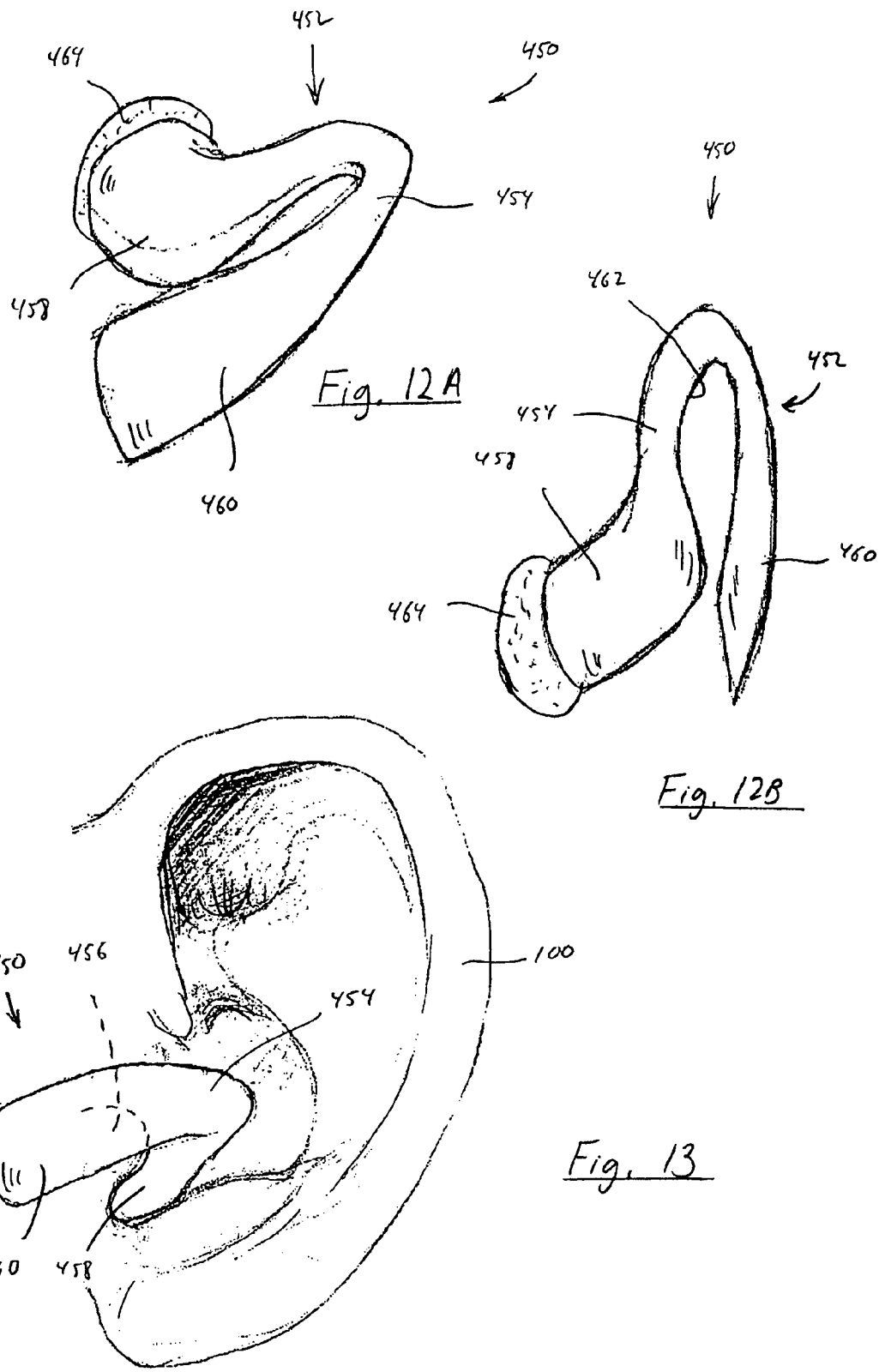

VESTIBULAR SYSTEM STIMULATION APPARATUS

CROSS-REFERENCE TO RELATED APPLICATIONS

This application claims priority under 35 U.S.C. §119(e) from provisional U.S. patent application No. 60/642,367 filed Jan. 7, 2005, the contents of which are incorporated herein by reference.

BACKGROUND OF THE INVENTION

1. Field of the Invention

The present invention relates to an apparatus for stimulating the vestibular system, and, in particular, to a non-invasive stimulation electrode assembly having a portion that fits within the ear canal to stimulate the vestibular system and to a system using such an electrode assembly.

2. Description of the Related Art

The vestibular system is responsible for the detection of the position and motion of the head in space. The semicircular canals, which are located in the inner ear, are the sensory organs of the vestibular system, and collect head position and motion information and transmit it to the central nervous system via the eighth cranial nerve. Disorders of the vestibular system may result in physiological disorders such as dizziness, vertigo, and nausea, with symptoms ranging in severity from mild to completely debilitating.

Stimulation of either the semicircular canals, the utricle, saccule, or other otolith organs, as well as stimulation of the nerve fibers leading from these organs or the eighth cranial nerve, or combinations thereof result in a sensation of movement in normal subjects. Moderate stimulation of the vestibular system may cause perceptions of mild movement that are not unpleasant, but can have beneficial properties, such as promoting a sleep state in a patient.

Many techniques for stimulating the vestibular system exist. These methods include calorimetric, chemical, and electrical approaches. Calorimetric and chemical stimulation typically take the form of direct application of a warm solution or a chemical compound, either directly or indirectly, to the eighth cranial nerve. Electrical stimulation of the vestibular system typically includes the placement of an electrode on the surface of the skin, e.g., over the mastoid bone behind the ear, or the piercing of the tympanic membrane with an electrode for direct stimulation of the semicircular canals. It is also known to stimulate the vestibular system by invasive electrodes implanted within the inner ear.

Stimulation of the vestibular system via a surface electrode often causes non-specific activation of nerves and muscles that result in unpleasant experiences for the patient. For example, surface electrode stimulation of the vestibular system may result in non-specific activation of facial muscles and/or the auditory aspect of the eighth cranial nerve, causing involuntary twitches and auditory perceptions, respectively. While direct electrode stimulation of the semi-circular canals is specific, the placement of an electrode through the tympanic membrane and/or within the inner ear can be quite unpleasant for the patient, and also presents an opportunity for infection of or physical damage to the inner ear, tympanic membrane, or other components of the ear.

Thus, a long standing need exists within the medical field for a system that allows for the specific and non-invasive activation of the vestibular system that is comfortable enough for a patient to wear for an extended period time, such as during sleep, and during periods of quiet resting. In addition, such a system should allow for the delivery of a wide variety of stimulation frequencies and waveforms to the vestibular system of the inner ear. The system should also be comfortable for the patient even when the system is disposed between the patient and an underlying support, for example when the patient's head is lying on a pillow with the stimulation system situated between the head and pillow. In addition, the system should remain firmly in place so that the stimulating energy is delivered to the desired anatomical location despite normal movement and contact forces, such as tossing and turning during sleep and when attempting to fall asleep.

SUMMARY OF THE INVENTION

Accordingly, it is an object of the present invention to provide an apparatus for the non-invasive and specific activation of the vestibular system in a patient that overcomes the disadvantages associated with conventional vestibular stimulation techniques. This object is achieved by providing an apparatus for delivering electrical stimulation to a vestibular system of a patient that includes a body member and a stimulating electrode coupled to the body member. In one exemplary embodiment, the body member is sized and configured such that it remains outside the user's ear canal. The stimulating electrode is formed, at least in part, from a deformable material that is sized and configured such that at least a portion of the deformable material rests against a surface within an ear canal of the user when the apparatus is properly positioned on such a user.

In a further exemplary embodiment of the present invention, the deformable material is a porous material and an electrolytic substance is disposed in at least a portion of the porous material. The present invention also contemplates providing a reservoir of electrolytic solution that is integral to or associated with the structure that supports the stimulating electrode. The present invention also contemplates that the stimulating electrode is a porous conductive material, eliminating the need for an electrolytic substance.

The stimulating electrode operates in conjunction with a stimulation unit that is capable of generating an electrical signal. The electrical signal is delivered to the vestibular system via the stimulating electrode. In one type of stimulation therapy, the electrical signal is a sine wave. The stimulation unit can be remote from or part of the body member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 6A-6D show four alternative embodiments for the electrode assembly according to the principles of the present invention;

FIGS. 12A and 12B are front and top perspective views, respectively, of a tenth embodiment for the electrode assembly according to the principles of the present invention; and FIG. 13 is a side view of a human ear showing an approximate location of the electrode stimulating system of the present invention of FIG. 11 attached to the tragus.

DETAILED DESCRIPTION OF THE PRESENTLY

Preferred Embodiments of the Invention

Figure 1:
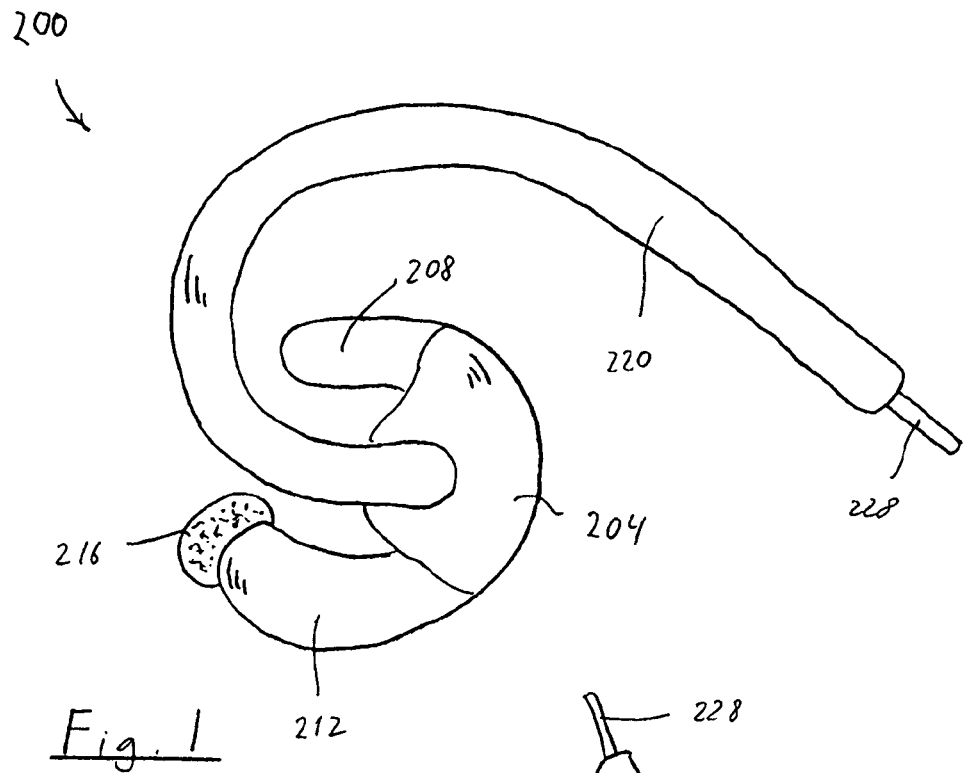
FIG. 1 is a side view of an electrode assembly for stimulating the vestibular system according to the principles of the present invention.
Figure 2:
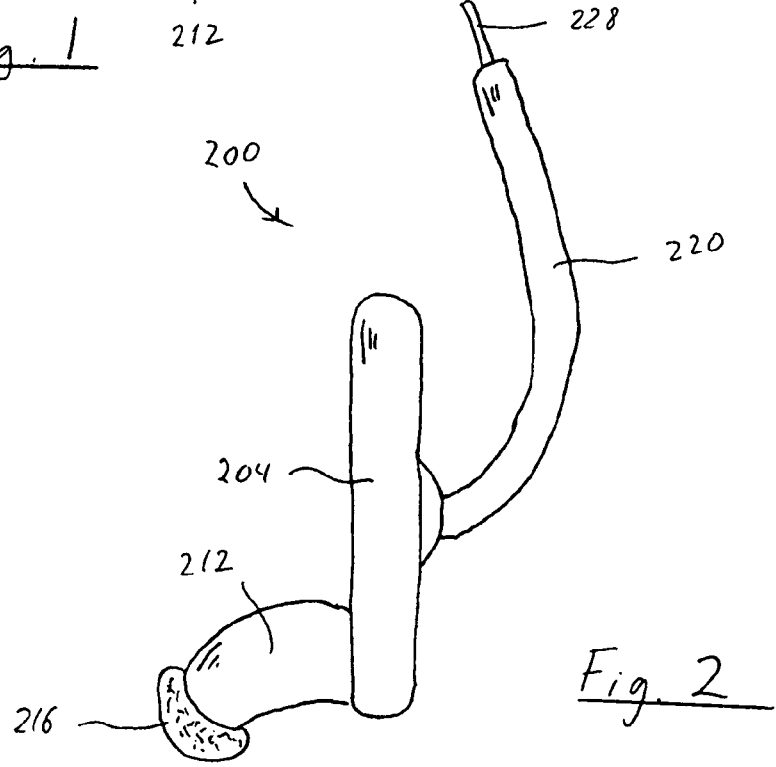
FIG. 2 is a front view of the electrode assembly of FIG. 1.
Figure 3:
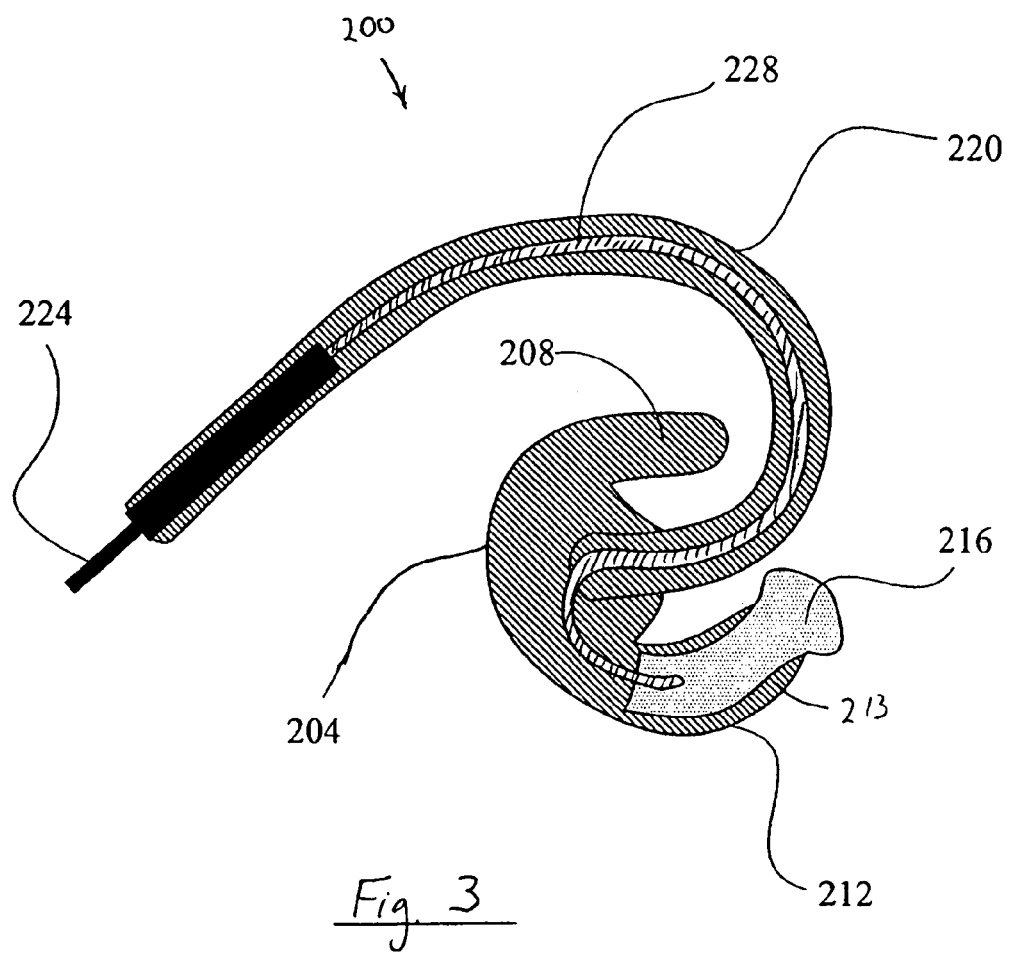
FIG. 3 is a cross-sectional side view of the electrode assembly of FIG. 1.

The present invention contemplates implementing the vestibular stimulation electrode assembly in a variety of different embodiments. However, some characteristics of the electrode assembly are common to all embodiments. For example, the vestibular stimulating electrode assembly of the present invention is placed, at least partially, in the ear canal of the user such that a surface of the stimulating electrode is directly in contact with the surface of the ear canal. As a result, a low-resistance electrical contact is established between the skin of the interior of the ear canal and the stimulating electrode. The stimulating electrode is generally contoured or configurable so as to fit comfortably within the ear canal. The stimulating electrode is supported by a structure, embodiments of which will be described more fully below, so that its placement remains relatively stable while in the ear canal. The support structure of the present invention also preferably provides for the ability to provide for an electrical lead that runs from the stimulating electrode to a stimulation apparatus.

In the presently-preferred embodiments, the stimulating electrode is supported by a body member that has several general characteristics. First, the body member supports the stimulating electrode such that the electrode maintains contact with the skin of the patient when worn by the user. In addition, the body member shields the user from any electrical wires or other structures that may irritate the skin. The body member also rests in, on, or near the ear lightly and comfortably so that it may be worn for prolonged periods of time, such as during sleep. The body member is constructed from a bio-compatible substance so that it does not irritate the user's skin.

The stimulating electrode that is coupled to the body member of the electrode assembly is preferably composed of a bio-compatible material so as to not irritate the skin of the patient. The present invention contemplates that the stimulating electrode is either composed of a conductive media, e.g., a conductive gel or hydrogel, or metallic electrode, or is composed of a substance that is capable of being saturated with a conductive media, e.g., a foam saturated with electrolytic solution. The present invention further contemplates that the stimulating electrode is composed of material that is conformable or expandable so that the stimulating electrode can mold to the portion of the ear that it is contacting. This attribute allows the stimulating electrode to maintain more consistent physical and, thus electrical, contact with the skin of the patient.

The stimulating electrode is employed to stimulate the vestibular system of the inner ear electrically by passing stimulating energy in the form of an electrical current to the vestibular system. The stimulation of the vestibular nerve is known to be frequency dependent. As such, the present invention allows for the stimulation of the vestibular system across a frequency range. The exact frequency of stimulation may be determined on a individual basis for each patient. The apparatuses and methods of the present invention are useful in the treatment of such disorders as insomnia, vertigo, sea sickness, and sleep apnea. Examples of the uses for stimulating vestibular system are described in U.S. Pat. No. 6,314,324 to Lattner et al.

A better understanding of the present invention may be gained by a detailed description of the following presently-preferred embodiments of the present invention, which are discussed below with reference to FIGS. 1-5. These figures illustrate a first exemplary embodiment of a vestibular stimulation electrode assembly 200 according to the principles of the present invention. Vestibular stimulation electrode assembly 200 includes a main body member 204, which is preferably composed of a bio-compatible material that is flexible, e.g., silicone, so as to allow flexibility in fitting the body member into the ear.

The human ear has an outer or external portion referred to as a pinna 100. Generally centrally located on the pinna is a deep, capacious cavity referred to as the concha 102. An ear canal 104 is located at the concha. Main body member 204 of vestibular stimulation electrode assembly 200 is sized and configured to rest within concha 102, much like as a hearing aid or ear plug. This is perhaps best shown in FIGS. 4 and 5. Body member 204 can be sized and configured to substantially block the ear canal, for example to reduce the amount of sound carried to the ear drum. This may be particularly advantageous in situations where the vestibular stimulating system is being worn during sleep or restful periods. Conversely, the body member can be sized and configured so that sound can enter the ear canal relatively unimpeded.

In the illustrated embodiment, vestibular stimulation electrode assembly 200 includes a first protrusion 208 that is either integral with the body member or attached thereto. First protrusion 208 is preferably soft and relatively flexible so that the vestibular stimulating system can conform into any individual's ear without the apparatus needing to be custom fit for each individual. In the illustrated exemplary embodiment, the body member is sized and configured to fit within a cavum conchae 110 of a concha of a patient's pinna, and the first protrusion is flexible, sized, and configured to fit within a cymba conchae 112 of the concha of such a patient's pinna. The concha is partially divided into two parts by the crux or commencement 114 of the helix. The upper part is termed the cymba conchae, and the lower part the cavum conchae.

Vestibular stimulation electrode assembly 200 further includes a second protrusion 212 having a first end portion coupled to body member 204 and a second end portion 213 that is distal from the body member. The second protrusion is sized and configured to fit within ear canal 104 of the patient. Like the first protrusion, second protrusion 212 is preferably relatively soft and flexible so it can conform to fit into any individual's ear canal without the apparatus needing to be fit for each individual. Preferably, the second protrusion is shaped so that in its natural, or non-deflected, position, it corresponds generally to the shape of the outer portion of the human ear canal. In addition, second protrusion 212 extends at an angle away from the main plane of body member 204 so that it is readily insertable into the ear canal. Second protrusion 212 is either integral with the body member or attached thereto.

Coupled to second end portion 213 of second protrusion 212 is a stimulating electrode 216 that is used to deliver stimulating energy to a vestibular system 108 of the patient. Stimulating electrode 216 can have any one of a variety of configurations so long as it provides an electrical contact with the surface of the user. Preferably, stimulating electrode 216 is composed of a deformable substance that allows the tip of the stimulating electrode to conform to the skin of the ear canal, thus establishing a consistent electrical contact with the surface of the patient. Stimulating electrode 216 is coupled to second protrusion 212 in any conventional manner, such as by means of an adhesive, molecular bonding (such a molding the two materials together), or via mechanical couplings. Preferably, a receiving notch is provided in the distal end of the second protrusion into which the stimulating electrode inserts or is fitted.

In a first exemplary embodiment of the present invention, the stimulating electrode is composed of a conductive gel or hydrogel. Using conductive gel for the stimulating electrode provides relatively good electrical conductivity, and it allows the shape of the electrode to deform and recoil, so that the electrode is easily and comfortably positioned in the ear canal while still providing a relatively large surface-to-surface contact with the user.

In another embodiment, the stimulating electrode is composed of a conductive porous, deformable material, such as a foam that is coated with a conductor. The conductor can be provided only on the outer surface of the foam or all throughout the foam. An all metallic electrode that contains pores can also be used, rather than a non-metallic material that is coated with a conductor. An example of such an electrode would have a structural configuration similar to steel wool.

In still another embodiment, the present invention contemplates that stimulating electrode 216 is composed, at least in part, of a porous hydrophobic material that is saturated with an electrolytic gel or solution. The porous hydrophobic material can be an open cell structure or a closed cell material configured to retain the electrolytic fluid in the cells to provide a good electrical contact with the surface of the user. In an exemplary embodiment, the porous hydrophobic material is a foam. An example of an open cell hydrophobic foam suitable for use as the porous material of the present invention is the Polyform Viscoelastic Foam sold by Polymer Technology, Inc. of Delaware.

Yet another embodiment of the present invention contemplates that the stimulating electrode is formed, at least in part, from a porous hydrophillic material. As with the hydrophobic structure, the porous hydrophilic material can be an open cell or a closed cell material. A hydrophilic material is particularly desirable for use as the electrode because it has surfaces and walls that wick and absorb liquid. An example of an open cell hydrophilic foam suitable for use as the porous material of the present invention is the Polydamp® Acoustic Foam also sold by Polymer Technology, Inc. Examples of other hydrophilic materials suitable for use as the porous material include, but are not limited to felt, cotton, foam, and any material that is capable of wicking a fluid.

A hydrophilic open or closed cell foam is a preferable material for use as the electrode material because it avoids biocompatibility problems and provides absorption of electrolytic solution with minimal expansion, thereby avoiding unneeded pressure in the ear. The absorption and wicking properties of the hydrophilic material also provides a conductive path and contact to the ear surface, requiring less retention force. That is, even as the electrolytic material, evaporates from the electrode material, the absorption and wicking properties of the hydrophilic material redistribute the remaining electrolytic material to provide an electrical contact with the surface of the user. These features of the present invention enhance the comfort of the stimulation apparatus because it allows the device to use a lower durometer silicone for the body, and requires less pressure in order to provide a good electrical contact with the user. In short, the use of a hydrophilic material and liquid state electrolyte make the electrode assembly of the present invention more comfortable and, hence, enhance user compliance with the treatment, than is conventionally available.

Open cell foams have holes or other passages that interconnect the cells. This is preferred when using an electrolytic fluid with a hydrophobic electrode material so that the fluid can maintain an electrically conductive path through the open cell structure. Closed cell foams do not have such passage, and are like a fused set of closed balloons, where the interior of each balloon is isolated from the interior of the other balloons. Examples, of materials suitable for use as the electrolytic fluid (gel or solution) include, but are not limited to the Signagel® Electrode Gel or the Signaspray® Electrode Solution & Skin Prep both of which are sold by Parker Laboratories, Inc. of New Jersey.

One advantage with using a hydrophilic or hydrophobic foam in combination with an electrolytic solution for the vestibular stimulation electrode assembly is that this permits the vestibular stimulation electrode assembly to be packaged and shipped dry, i.e., the electrolytic solution need not be disposed in the porous material when it is originally packaged. This simplifies the manufacture and shipping of the vestibular stimulation electrode assembly. For example, the electrolytic solution can be shipped in its own container separate from the electrode assembly containing the hydrophilic or hydrophobic foam. The electrolytic solution can be introduced to or added to the electrode assembly as needed by the user. This method could also extend the useable life of the electrode assembly by allowing the user to let the stimulating electrodes dry between uses, and then "renew" the electrode when desired by re-applying the electrolytic fluid to the electrode assembly before using the vestibular stimulation therapy.

A bulbous head at the distal part of the stimulating electrode further enhances the ability of the deformable electrode to contact the surface of the patient. It is to be understood, of course, that the present invention contemplates that the stimulating electrode can have a variety of configurations, shapes, sizes, and physical properties, such as various degrees of electrical or head conductivity, density, porosity, so as to achieve any goal desired for the stimulating electrode, such as sound transmission, reduction or enhancement, and heat dissipation or insulation.

In the illustrated exemplary embodiment, an insulated electrical wire 228 is connected to stimulating electrode 216. The present invention contemplates connecting insulated electrical wire 228 to stimulating electrode 216 using any number of techniques including, but not limited to: fusing the wire with stimulating electrode 216, wrapping the wire around the foam of stimulating electrode 216, and an inserting the insulated wire directly into the stimulating electrode. One of skill in the art will recognize there are many appropriate ways to connect insulated wire 228 to stimulating electrode 216. Insulated wire 228 extends down a wire lead 220 to an electrical connector 224. Wire lead 220 is preferably flexible and formed form bio-compatible substance, such as, but not limited, to silicone, that surrounds wire 228.

Figure 5:
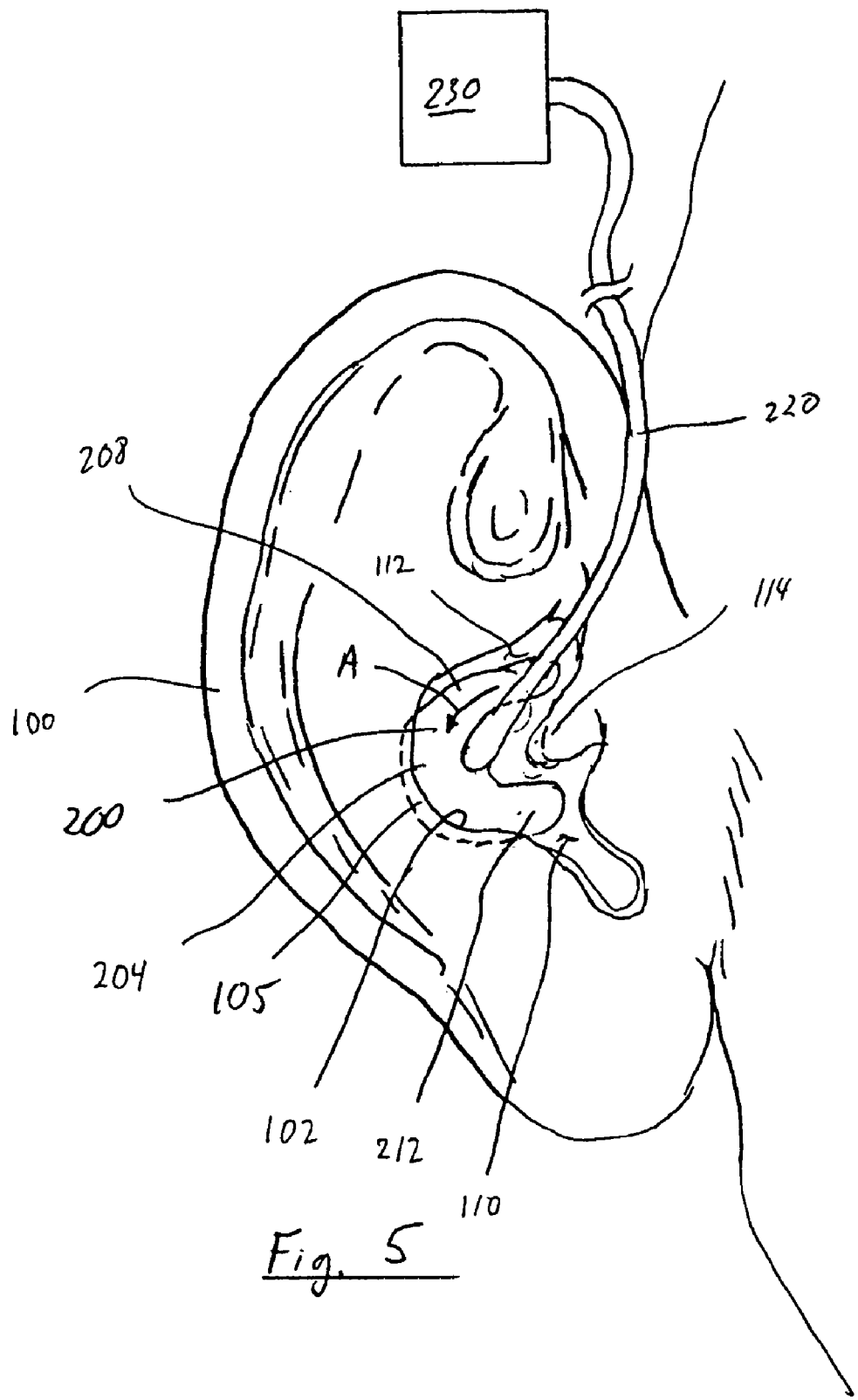
FIG. 5 is a side view of a human ear showing an approximate location of the electrode stimulating system of the present invention on the patient, and schematically illustrating an external stimulating energy control system.

As shown in FIG. 5, the electrical wire connects the vestibular stimulation electrode assembly to a stimulating system 230. The electrical connectors allows vestibular stimulating apparatus 200 to be detachable from the remaining components of the stimulation system. This embodiment of the present invention shows a standard male electrical connector 224. However, one of skill in the art would recognize that any one of a number of electrical connectors could be used in this capacity.

Stimulating system 230 is any system capable of providing an energy to the stimulating electrode. It can be appreciated that the purpose of providing the stimulating energy can range from entertainment to medical therapies. A typical stimulating system includes a source of stimulating energy, such as any conventional power supply, and a controller to control the delivery of the stimulating energy to the stimulating electrode. The stimulating system can also include sensors or other means for gathering feedback information used by the controller in controlling the delivery of the stimulating energy to the stimulating electrode.

Figure 4:
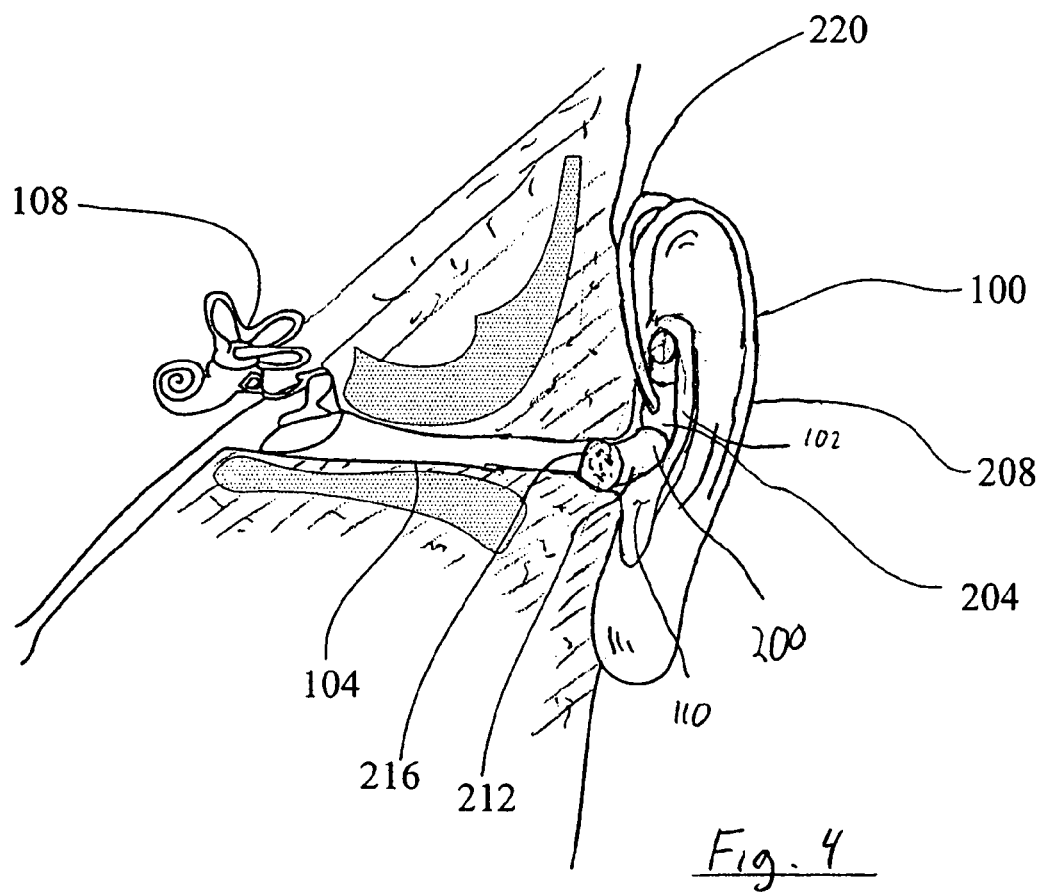
FIG. 4 is a cross-sectional diagram of the human ear showing the approximate location of the electrode stimulating system of the present invention on the patient.

FIGS. 4 and 5 illustrate the approximate location of a presently-preferred embodiment for vestibular stimulation electrode assembly 200 of the present invention within the ear of a patient. Vestibular stimulation electrode assembly 200 is shown resting snugly in the folds of the external ear 100 or pinna. First protrusion 208 presses or rests against the folds of the external ear 100 to enhance the fit of the electrode assembly to the user. Second protrusion 212 is shown protruding into ear canal 104. Stimulating electrode 216 preferably rests in and establishes electrical contact with the skin in ear canal 104. When a stimulating waveform is passed through the stimulating electrode 216, current is preferably distributed three-dimensionally through the patient's tissues and selectively activates or otherwise induces an effect upon vestibular system 108.

When properly positioned in the user's ear, vestibular stimulation electrode assembly 200 is disposed in concha 102 such that main body member 204 is in the cavum conchae and first protrusion 208 is disposed in the cymba conchae. The first protrusion is sized and configured to push against the cymba conchae such that a force is directed through the electrode assembly as generally indicated by arrow A in FIG. 5. By directing the force in this direction, the second protrusion of the electrode assembly is pushed securely into to ear canal, and, more specifically, against the surface of the user. The spiral-like or C-shape of the electrode assembly also contributes to the ability to control the direction of the force holding the electrode assembly in place. The electrode assembly is also preferably sized and configured such that the body member 204 underlies a flap of tissue 105 typically overlying the concha, further enhancing the ability of the electrode assembly to remain in place in the user's ear. Similarly, the present invention contemplates that first protrusion 208 is sized and configured to fit under a flap of tissue extending over a user's cymba conchae 112, also helping to keep the first protrusion snug within the ear.

FIGS. 6A-6D illustrate four presently-preferred alternative embodiments for the vestibular stimulation electrode assembly according to the principles of the present invention. FIG. 6A illustrates a vestibular stimulation electrode assembly 240 that includes a main body member 242 and a protrusion 212 that supports a stimulation electrode 216. This embodiment lacks the first protrusion present in the previous embodiment. Thus, this embodiment is more stream-lined than the previous embodiment.

FIG. 6B illustrates a vestibular stimulation electrode assembly 250 in which a first protrusion 252 is coupled to the body member and wherein the first protrusion includes a plurality of perforations or holes 254. These holes provide first protrusion 252 with a relatively high degree of flexibility so that the first protrusion easily and comfortably deforms to fit within the concha of the user. This embodiment represents a technique for providing a high degree of flexibility for the first protrusion by altering the mechanical structure for the protrusion rather than altering the composition of the first protrusion. Of course, the present invention contemplates forming the first protrusion from a highly flexible material in addition to or in place of providing structural features, such as holes, in that material to enhance its flexibility.

Yet another embodiment of a vestibular stimulation electrode assembly 260 according to the principles of the present invention is shown in FIG. 6C. In this embodiment, a first protrusion 262 connected to the body member has a scalloped portion along its length so as to provide the first protrusion with a relatively high degree of flexibility. In the illustrated embodiment, the scalloped portion is shown as a series of pleats 264, which can also be considered as flanges. It is to be understood that the present invention contemplates that the scalloped portion can have other configurations for the folds, pleats, or flanges that provide the flexibility to the first protrusion. For example, the scalloped portion can have a bellows-like configuration or the individual pleats can be more rounded to maximize patient comfort.

FIG. 6D shows still another embodiment for a vestibular stimulation electrode assembly 270 according to the principles of the present invention. In this embodiment, first protrusion 272 includes both a plurality of perforations or holes 274 and a scalloped portion 276 along its length. Again, the specific size and configuration for the holes and the folds in the scalloped portion can vary.

During use, the porous material forming stimulating electrode 216 may dry out. That is, the electrolytic gel, fluid, or solution saturating the porous material may evaporate or otherwise be expelled form the porous material. Conversely, it may be preferable to leave the porous material unsaturated during packaging and shipping of the electrode assembly. In which case, a system is needed for easily and conveniently introducing or reintroducing the electrolytic material into the porous material.

Figure 7:
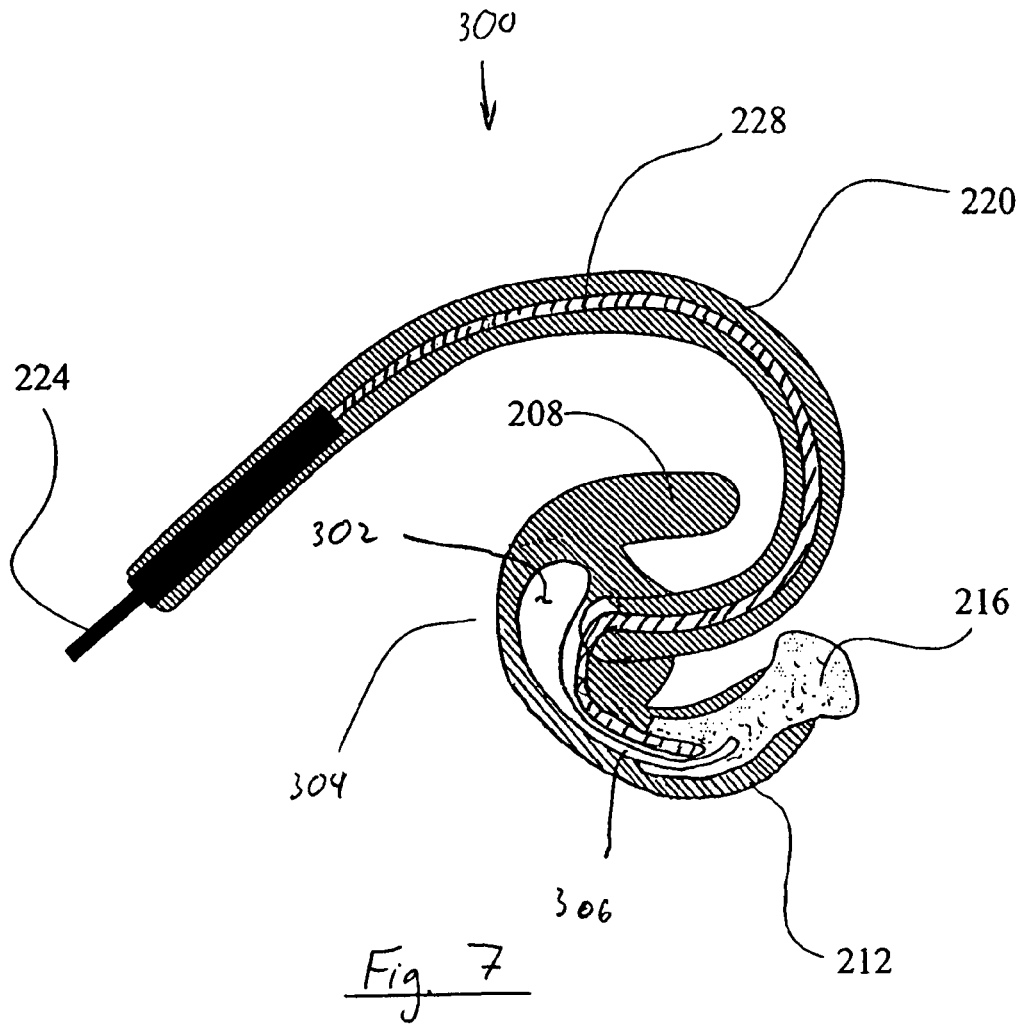
FIG. 7 is a cross sectional view of a fifth embodiment for the electrode assembly according to the principles of the present invention.

FIG. 7 illustrates a fifth embodiment for an electrode assembly 300 according to the principles of the present invention that accomplishes this function. In this embodiment, a bladder 302 is provided in body member 304 that stores the electrolytic substance. A channel 306 is provided from the bladder to stimulating electrode 216. The user dispenses the electrolytic substance stored in the bladder into the porous material by squeezing the bladder causing the electrolytic substance to be injected into the porous material. While the bladder is shown provided within the body member, the present invention also contemplates providing the bladder in first protrusion 208, second protrusion 212, or any combination thereof.

The present invention further contemplates removing the bladder from the electrode assembly but leaving an electrolytic substance filling channel defined from a portion of the electrode assembly to the porous material. A filling port (not shown) would have to be provided on the electrode assembly and coupled to the filling channel so that the electrolytic substance can be introduced into the porous material through the filling channel. This embodiment allows for easy filling or refilling of the electrolytic substance into the porous material using a less complicated filling arrangement. In addition, refill packages of the electrolytic substance can be provided, so that the electrode assembly can be reused multiple times. Of course, a filling port can also be provided so that bladder 302 can be refilled.

Figure 8:
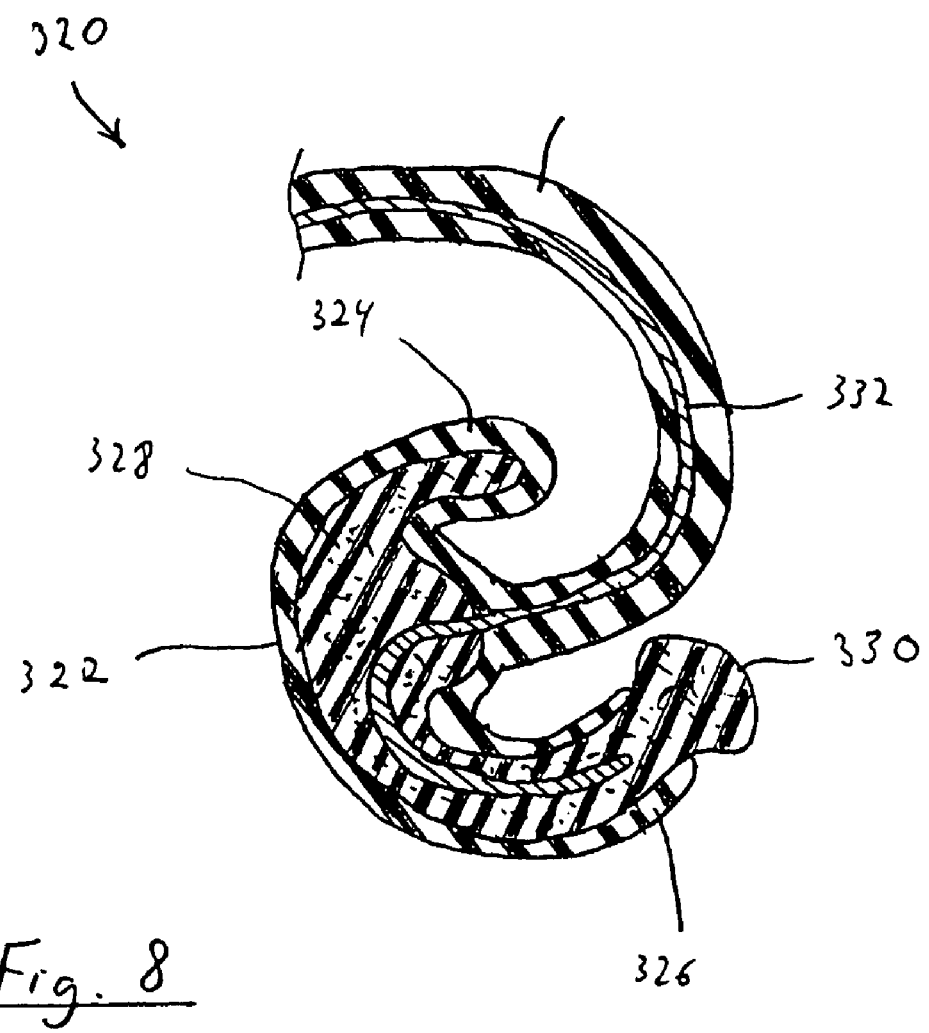
FIG. 8 is a cross-sectional view of a sixth embodiment of a vestibular stimulation electrode assembly according to the principles of the present invention.

FIG. 8 is a cross-sectional view of a sixth embodiment of a vestibular stimulation electrode assembly 320 according to the principles of the present invention. In this embodiment, body member 322, first protrusion 324, and second protrusion 326 are formed from a single piece of porous material 328 that also forms stimulating electrode 330. That is, a hot molding method is used to form a cured hydrophilic foam, which serves as the stimulating electrode, into the shape shown in the FIG. 8. The foam also defines the general overall shape for the entire electrode assembly. A lead wire 332 is fixed to the stimulating electrode. The body member, the first protrusion, and the second protrusion are formed by applying a coating of material to the outer surface of the porous material using any conventional process, such as a spraying or dipping type process. In a preferred embodiment, this outer coating of material is formed from a soft rubber, is an electrical insulator, and is water-proof.

The area of the porous material that forms the stimulating electrode needs to be exposed so that the therapy energy can be delivered to the patient. That is, the present invention contemplates providing the outer coating over the entire cured foam, and removing the portion of the outer coating where the stimulating electrode is to be located. This is accomplished by simply removing the outer coating covering this portion of the cured foam. Additionally, it is possible to prepare the mold prior to formation of the foam with a thin polymer film to coat and seal the outer surface of the foam when heat-formed.

The present invention contemplates strain releaving the wire within the foam body member. That is, pullout of wire 332 from electrode 330 is prevented using one or more techniques discussed below. According to one embodiment, an adhesive is applied at the junction where the wire attaches to the electrode, where the electrode joins the polymer, or both. This is accomplished, for example, by dipping the wire in an adhesive prior to inserting the wire into the electrode. The present invention also contemplates using mechanical features, such as barbs or other stopper type device disposed on the wire, to prevent pullout of the wire from the electrode. In addition, the outer coating makes the interface between the wire and the porous material more durable. A spray-on polymer coating can also be used as the outer coating.

The present invention also contemplates that a formulation of polymer that can be used, which will cure inside of a mold, expanding to form the shape of porous material 328. In this case, the mold would have a lead-wire laid into its cavity prior to the molding step. Strain relief, i.e., prevention of pullout of the wire from the electrode, is provided by the bond between the polymer and the electrode.

Figure 9A:
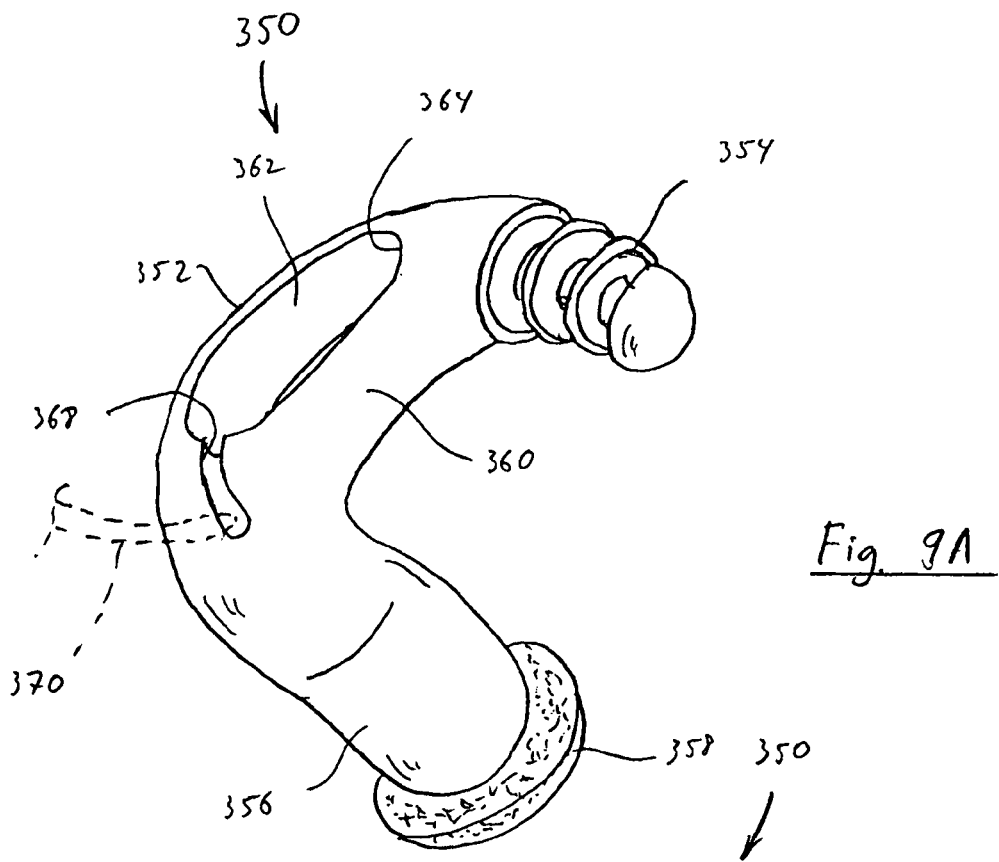
FIGS. 9A and 9B are perspective views of a seventh embodiment for the electrode assembly according to the principles of the present invention.
Figure 9B:
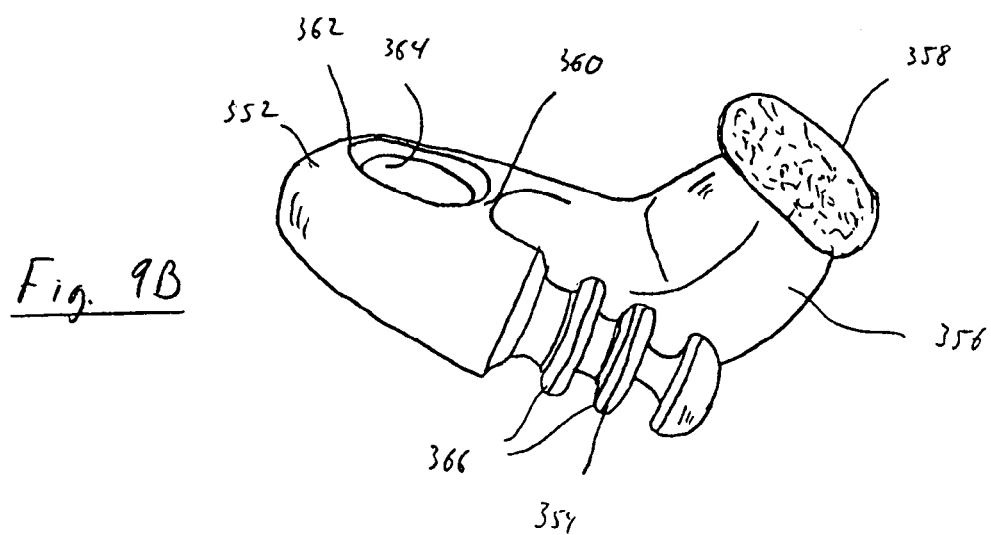

FIGS. 9A and 9B illustrate a seventh embodiment for an electrode assembly 350 according to the principles of the present invention. A prominent feature of this embodiment is the relatively large kidney shape for body member 352. A first arm 354 is provided at one end of the C-shaped body member, and a second arm 356 is provided at an opposite end of the body member. Stimulating electrode 358 is provided at the end of second arm 356.

The body member is preferably defined by a first limb 360 and a second limb 362 with an opening 364 defined between these two members. First limb 360 is preferably formed from a thin membrane, so that it easily deforms around the cartilage of the ear, namely around the crux, which separates the concha into upper and lower parts. When properly worn in the ear, first arm 354 fits in the cymba conchae, and the second arm 356 fits in the cavum conchae. Second limb 362 provides the strength to maintain the structure in the ear.

A distal end portion of first arm 354 includes a plurality of alternating sections 366 having large and small diameters. This configuration optimizes the flexing of the distal end of the first arm. It also provides the ability to easily alter the length of the first arm simply by, trimming sections 366 off of the first arm. A detent, slot, or groove 368 is provided in the body member to receive a wire 370. Detent 368 helps manage the wire by securing it to the body member and flush with the surface of the body member so that the wire does not entangle in other structures. Detent 368 also provides a stress relief for the wire.

The "C" shaped body member is advantageous in that the "C" shape body effectively functions as a type of spring, that applies pressure and compresses the stimulating electrode on the user's skin. This ensures a good electrical contact on the user.

Figure 10:
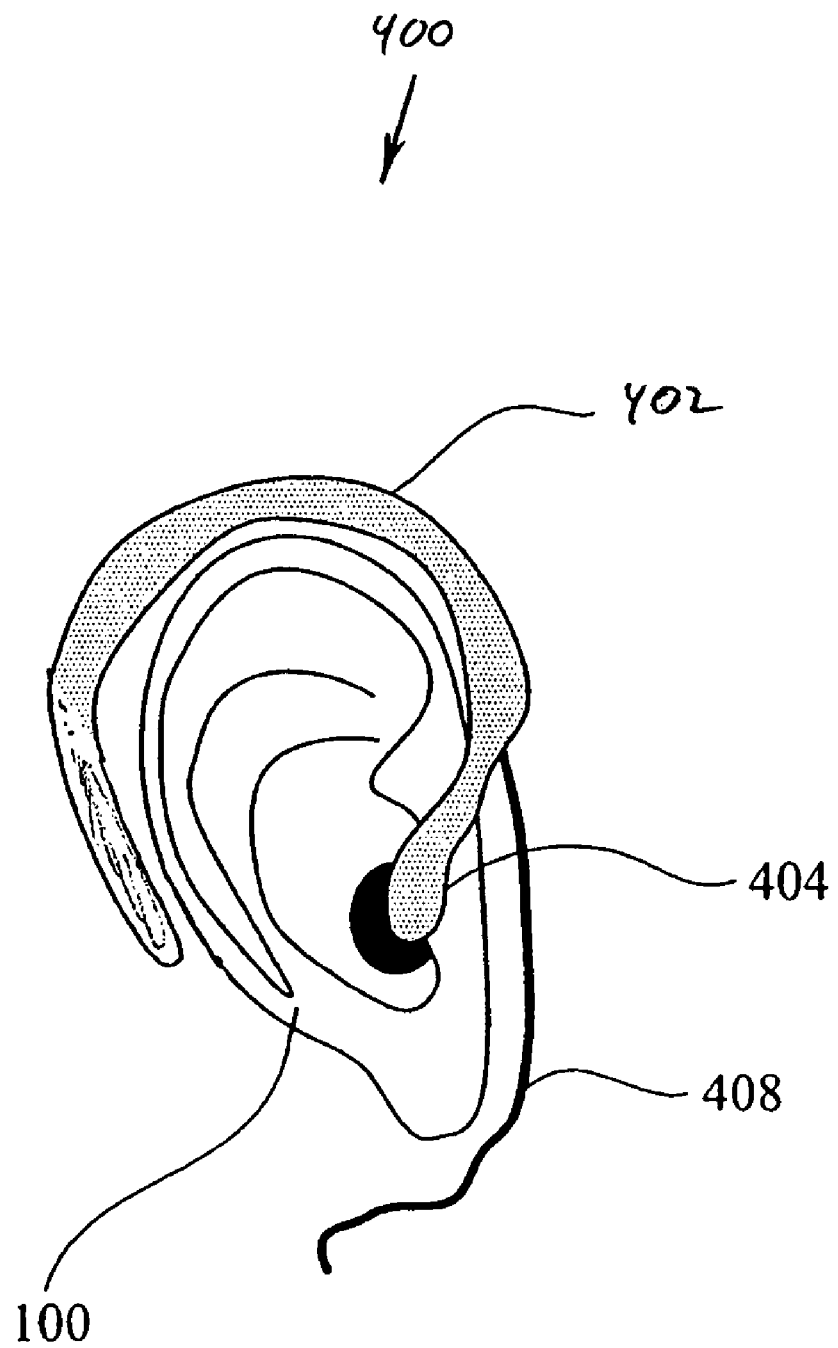
FIG. 10 is a side view of a human ear showing an approximate location of an eight embodiment of a electrode stimulating system of the present invention disposed around the human pinna.

FIG. 10 illustrates an eighth embodiment of a vestibular stimulation electrode assembly 400 according to the principles of the present invention and shown worn on a patient. Electrode assembly 400 includes a body member 402 that is sized and configured to fit around at least a portion of pinna 100. One end portion 404 of body member 402 is disposed in the concha and supports the stimulating electrode in the ear canal. The remainder of the body member wraps around the pinna. In the illustrated embodiment, a wire lead 408 is coupled to the body member and runs through at least a portion of the body member to the stimulating electrode, connecting the stimulating electrode to the stimulation energy supply system (not shown). The stimulating electrode is preferably formed in the same manner as the stimulating electrode discussed above.

Figure 11:
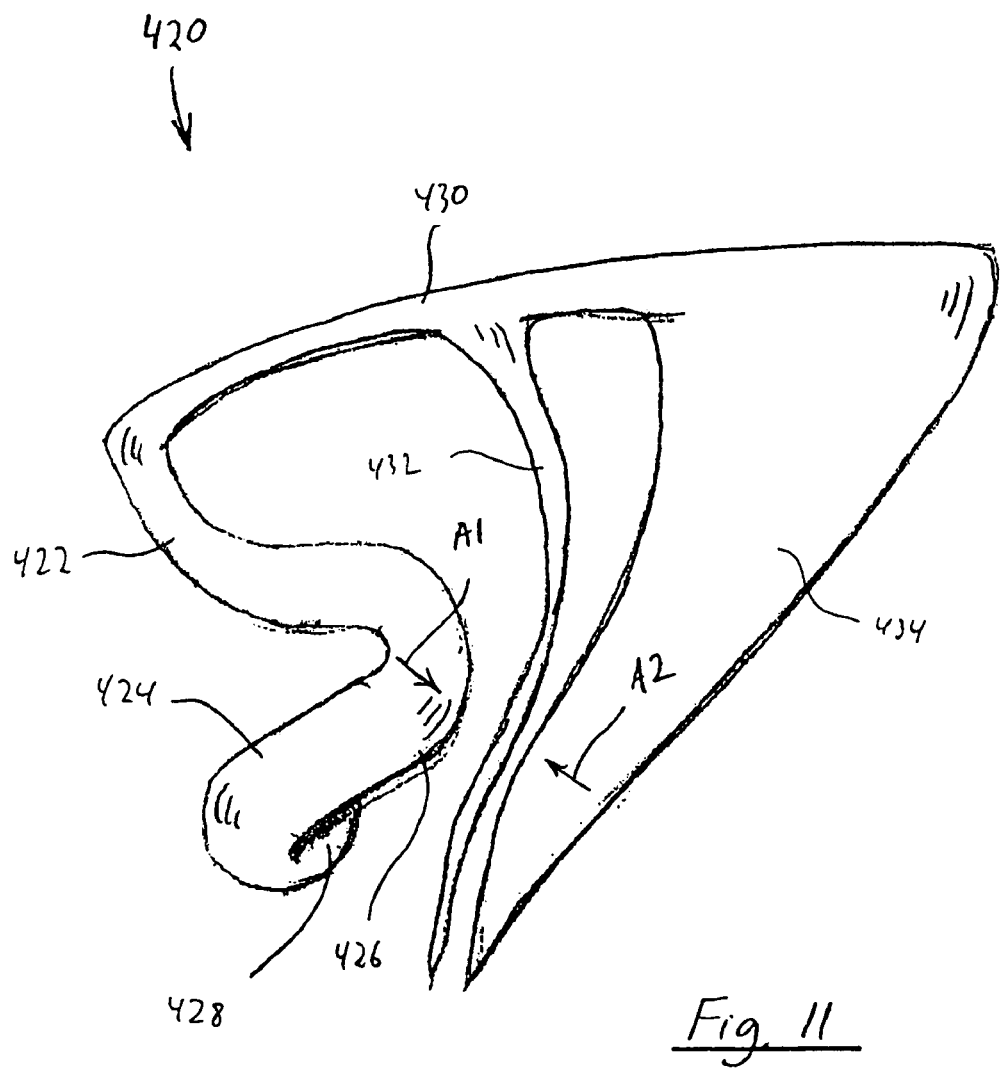
FIG. 11 a side view of a ninth embodiment for the electrode assembly according to the principles of the present invention.

FIG. 11 illustrates a ninth embodiment of vestibular stimulation electrode assembly 420 according to the principles of the present invention. Electrode assembly 420 is similar to electrode assembly 400 of FIG. 10 in that electrode assembly includes a body member 422 that that is sized and configured to fit around at least a portion of the pinna. In this embodiment, however, the body member functions as a "concha vice" by gently, yet firmly, pinching a portion of the pinna at the concha between portions of the body member to help hold the electrode assembly on the patient.

Body member 422 includes a first portion 424 that is adapted to fit within the patient's concha. First portion 424 includes a wall contacting portion 426 that contacts the wall of the concha. First portion 424 also includes a protruding portion 428 that inserts into the ear canal and supports the vestibular system stimulating electrode (not shown). It is to be understood that the stimulating electrode can have any of the above-described configurations.

Body member 422 includes a second portion 430 that extends out of the concha and around at least a portion of the pinna. Second portion 430 includes at least one member that fits behind the ear in juxtaposition with wall contact portion 426 so that the wall of the pinna is sandwiched between the portions of the body member. In the illustrated embodiment, a first arm 432, a second arm 434, or both are provided as portions of second portion 430 and serve this function. Body member 422 is configured such that first arm 432 and wall contact portion 426 are biased in directions indicated by arrows A1 and A2 to provide a pinching force on the wall of the concha.

It can be appreciated that the body member for the electrode assembly shown in this embodiment can have a variety of configurations and can be formed from any material suitable for use in the environment described above. The present invention contemplates that first arm 432 and second arm 434 are preferably relatively flat to maximize patient comfort in the event the user is lying on the side of his or her head with the electrode assembly under the head. The relatively large size for the portion of the body member that is outside of the pinna enhances the stability of the assembly. The present invention further contemplates that the body member be contoured to correspond, at least in general, to a portion of a human head near the pinna.

FIGS. 12A, 12B, and 13 illustrate a tenth embodiment for the electrode assembly 450 according to the principles of the present invention. Electrode assembly 450 includes a mechanism, generally indicated at 452, for attaching a body member 454 to a tragus 456 of a human ear. The tragus is a small pointed eminence in front of the concha that projecting backward over the concha. The body member is attached to the tragus by pinching the tragus between two portions of the electrode assembly. In the exemplary illustrated embodiment, these two portions of the electrode assembly are two parts of the body member: an internal portion 458 that fits underneath the tragus, and an external portion 460 that fits outside the tragus. A cavity 462 is defined between internal portion 458 and external portion 460 to receive at least a portion of the tragus. Internal portion 458 includes the structure that supports a stimulating electrode 464. It is to be understood that the stimulating electrode can have any of the above-described configurations. External portion 460 of body member 454 is flexible enough to allow it to fit around the tragus, but biased toward internal portion 458 such that the tragus is gently, yet firmly, pinched between the internal and external portions when the electrode assembly is worn on the ear.

While embodiment of the electrode assembly shown in FIGS. 12A-13 uses the body member as a bias spring to maintain a connection to the tragus, the present invention also contemplates that other techniques can be used to secure the electrode assembly to the tragus. For example, a clip similar to an earlobe clip used on a clip-on earring can be used to attached the body member to the tragus. In addition, the present invention contemplates using similar "clip-like" techniques to secure the body member of the electrode assembly to any portion of the pinna, including the ear lobe, so long as the stimulating electrode is disposed in the ear canal.

It can be appreciated that the wire connected to the electrode assembly has been omitted from the embodiments shown in FIGS. 10-13. However, the present invention contemplates that the wire can be connected to any portion of the body member. In addition, the electrode assembly can carry various components of the stimulation system, such as the power supply and the energy controller, that controls the delivery of the energy from the power supply to the stimulating electrode. In which case, an external electrical connection, i.e., a wire, would not be needed.

The embodiments described above show a single three-dimensional stimulation electrode placed in the ear canal of the patient. It is to be understood that the body member or other portions of the electrode assembly can support more than one electrode. For example, an additional electrode can be supported in the ear canal with the first electrode, or it can be supported at other locations on, in, or near the ear. This second electrode can serve, for example, as the reference electrode for the stimulating current applied to the patient.

The present invention also contemplates that the vestibular stimulation electrode assemblies described herein can be used conjunction with other patient interactive devices. For example, a speaker can be provided on the body member of the electrode assembly to deliver sounds, such as music, white noise, or noise cancellation energy to the inner ear.

The present invention also contemplates providing other monitoring devices on the electrode assembly, either inside or outside the ear canal. For example, U.S. Pat. No. 6,253,871 teaches an in-the-ear monitor for monitoring one or more vital signs of a user. The monitoring systems and techniques used in this patent, can be incorporated in the electrode assembly of the present invention, for example by providing the sensors taught by this patent on protrusion 212. An example of a further monitor is a temperature sensor, as it is known to measure body temperature through the ear.

The present invention also contemplates that the body member, the first protrusion, the second protrusion, or any combination thereof is moldable so that it can be shaped to match the features of the user's ear. In a further embodiment, body member, the first protrusion, the second protrusion, or any combination thereof is capable of maintaining that shape once so molded, i.e., is customizable to the features of the user.

In addition, the present invention contemplates providing an apparatus to detect the inner ear pressure as part of the electrode assembly. The present invention contemplates that such a pressure sensing device includes a flexible chamber containing a fluid, such as air or saline, with a pressure sensing device in communication with the flexible chamber. The flexible chamber is located in the ear canal, for example, by including it on protrusion 212, such that changes in pressure in the eustachian tube are detected by the pressure sensor associated with the flexible chamber. These changes in pressure in the eustachain tube can be correlated to caridio and/or pulmonary events.

It is to be understood, that in these latter embodiments, where monitoring capabilities are included with the electrode assembly, data collection, analysis, and communication devices can be provided in operative communication with the monitoring sensors. These other devices can be carried on or can be separate from the electrode assembly.

By specifically stimulating the vestibular system, the present invention may be used in the treatment of a variety of disorders. For example, the vestibular system may be stimulated using the apparatuses and methods of the present system to induce a rocking sensation in a patient. Such rocking may be useful for allowing a patient with insomnia to fall asleep. Alternatively, the present apparatuses and methods could stimulate the vestibular system to alleviate the symptoms of vertigo, sleep apnea, or dizziness.

Finally, the present invention contemplates that the electrode assembly can be used alone or in combination with other elements to provide the desired stimulation to the patient's vestibular system. For example, the present invention contemplates implanting passive elements, such as a inductance wire or electro/magnetic field focusing element in the patient at or near the vestibular system. The stimulating energy produced by the electrode assembly can be focused or otherwise altered or enhanced by such elements to provide the desired stimulation. In addition, the present invention contemplates providing one or more active stimulating elements, such as microstimulators, that are activated or powered by the energy provided by the stimulating system of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus for stimulating a vestibular system of a user, comprising:
   (a) a body member having an external surface formed to sit at least partially within a concha of an ear of a user during use to stimulate the vestibular system of the user, the body member having a portion of an electrolytic substance stored inside the external surface; and
   (b) a stimulating electrode coupled to the body member such that if the body member is seated in the concha of the ear of the user for use the stimulating electrode contacts a surface of an ear canal of the user, wherein the stimulating electrode includes a deformable, porous material that is sized and configured such that, during use to stimulate the vestibular system of the user, at least a portion of the deformable material rests against the surface of the ear canal, and wherein the stimulating electrode is in fluid communication with the interior of the body member such that the portion of the electrolytic substance stored inside the external surface is dispensed into the stimulating electrode such that electrical energy is carried to the surface of the ear canal through the stimulating electrode via the porous material.

2. The apparatus of claim 1, further comprising a bladder formed within the body member inside of the external surface of the body member that holds the portion of the electrolytic substance stored inside the external surface of the body member.

3. The apparatus of claim 1, wherein the porous material comprises a hydrophilic material or a hydrophobic material.

4. The apparatus of claim 1, wherein the body member is formed in part from a porous material encased by the external surface of the body member.

5. The apparatus of claim 4, further comprising a first protrusion coupled to the body member and extending therefrom, wherein the body member is sized and configured to fit within a cavum conchae of a concha of a user's pinna, and the first protrusion is flexible and sized and configured to fit within a cymba conchae of the concha of such a user's pinna.

6. The apparatus of claim 5, further comprising a second protrusion having a first end portion coupled to the body member and a second end portion, wherein the second protrusion is sized and configured such that the second end portion fits within the ear canal of such a user, and wherein the electrode is disposed on the second end portion of the second protrusion.

7. The apparatus of claim 1, wherein the body member is C-shaped having a central portion, a first arm having a proximal end coupled to a first end of the central portion, and a second arm coupled to a second end of the central portion, and wherein the stimulating electrode is disposed on a distal end of the first arm.

8. The apparatus of claim 1, wherein the body member is sized and configured to fit around at least a portion of an exterior of the pinna.

9. The apparatus of claim 1, further comprising attaching means for selectively securing the body member to a tragus of such a user.

10. A system for stimulating a vestibular system of a user, comprising:
   (a) a vestibular stimulation source configured to generate stimulating energy targeting neurons of a vestibular system of a user to induce a predetermined effect on the vestibular system; and
   (b) an electrode assembly electronically coupled with the vestibular stimulation source, the electrode assembly comprising:
      (1) a body member, and
      (2) a stimulating electrode coupled to the body member, wherein the stimulating electrode includes a deformable material that is sized and configured such that at least a portion of the deformable material rests against a surface within an ear canal of such a user responsive to the apparatus being positioned on such a user, the stimulating electrode being formed from one or more materials operable to communicate the stimulating energy generated by the vestibular stimulation source to the surface within the ear canal of the user.

11. The system of claim 10, wherein the source of stimulating energy is remote from the electrode assembly, and further comprising a hardwire connection operatively coupling the source of stimulating energy and the stimulating electrode.

12. The system of claim 10, wherein the source of stimulating energy is disposed on the body member of the electrode assembly.

13. The system of claim 10, wherein the stimulating electrode comprises a porous material.

14. The system of claim 13, wherein the stimulating electrode comprises an electrolytic substance disposed in at least a portion of the porous material.

15. The system of claim 10, wherein the stimulating electrode comprises a hydrophilic material or a hydrophobic material.

16. The system of claim 10, wherein the body member is sized and configured to fit within at least a portion of a concha of a user's pinna.

17. The system of claim 16, further comprising a first protrusion coupled to the body member and extending therefrom, wherein the body member is sized and configured to fit within a cavum conchae of a concha of a user's pinna, and the first protrusion is flexible and sized and configured to fit within a cymba conchae of the concha of such a user's pinna.

18. The system of claim 16, wherein the body member is C-shaped having a central portion, a first arm having a proximal end coupled to a first end of the central portion, and a second arm coupled to a second end of the central portion, and wherein the electrode is disposed on a distal end of the first arm.

* * * * *